(12) United States Patent
Jährling

(10) Patent No.: US 7,264,396 B2
(45) Date of Patent: Sep. 4, 2007

(54) SYSTEM FOR MEDICAL EMERGENCY CARE AND MONITORING OF A PATIENT

(75) Inventor: Peter Jährling, Puschendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/386,282

(22) Filed: Mar. 11, 2003

(65) Prior Publication Data

US 2004/0001571 A1 Jan. 1, 2004

(30) Foreign Application Priority Data

Mar. 13, 2002 (DE) ................ 102 11 081

(51) Int. Cl.
*A61B 6/04* (2006.01)
(52) U.S. Cl. ............... 378/195; 378/20; 378/196; 378/209
(58) Field of Classification Search ........... 378/20, 378/193, 195, 196, 197, 198, 204, 208, 209; 600/427; 5/601
See application file for complete search history.

(56) References Cited

U.S. PATENT DOCUMENTS

| 5,327,474 | A | * | 7/1994 | Inoue et al. ............. 378/196 |
| 5,475,884 | A | * | 12/1995 | Kirmse et al. ............ 378/209 |
| 5,661,772 | A | | 8/1997 | Bär et al. |
| 5,822,814 | A | | 10/1998 | Van der Ende |
| 6,212,251 | B1 | * | 4/2001 | Tomura et al. ............. 378/195 |
| 6,302,579 | B1 | | 10/2001 | Meyer et al. |
| 6,304,627 | B1 | | 10/2001 | Horbaschek |
| 6,364,526 | B2 | * | 4/2002 | Ivan et al. ................. 378/198 |
| 6,869,217 | B2 | * | 3/2005 | Rasche et al. ............. 378/197 |

FOREIGN PATENT DOCUMENTS

| CN | 2164817 Y | | 5/1994 |
| DE | 19908494 A1 | * | 10/2000 |
| JP | 06047040 A | * | 2/1994 |

OTHER PUBLICATIONS

Siemens -Prospekt "SOMATOM Emotion, Balance, Esprit—Sliding Gantry", Nr. A91001-M2120-G151-01-7900.

* cited by examiner

*Primary Examiner*—Chih-Cheng Glen Kao
(74) *Attorney, Agent, or Firm*—Brinks Hofer Gilson & Lione

(57) ABSTRACT

A system for medical emergency care and monitoring of a patient includes as its first component a patient holding apparatus with a fixed base and a table mounted on it, and the table protrudes past the base on the head end with a radio transparent first region and on the foot end with a radio transparent second region. There is also a CT scanner which is movable on the floor along a guide element in such a way that the second region of the table can be brought, by moving the CT scanner, into the patient opening of the CT scanner. For taking x-ray images in the first region of the table, there is an x-ray unit. Another component pertains to a guided patient board that is ridable on the table in the longitudinal direction.

20 Claims, 4 Drawing Sheets

SYSTEM FOR MEDICAL EMERGENCY CARE AND MONITORING OF A PATIENT

REFERENCE TO RELATED APPLICATIONS

The present patent document claims priority to German Application Serial No. DE 10211081.6, filed Mar. 13, 2002, which is hereby incorporated by reference.

BACKGROUND

The invention relates to a system for medical emergency care and monitoring of a patient.

In the diagnosis and treatment of critically injured patients, severely injured patients, or patients with multiple traumas, there is a need to be able to perform clinical processes within a very short time in order to minimize lasting damage to the patient and thus to minimize clinical follow-up and health care costs.

Typically, the patient is taken by emergency technicians to a so-called trauma room, where he is first physiologically stabilized by life-support measures. In some places, the first information on possible internal injuries is also collected using an ultrasound apparatus. After that, the patient is taken to radiology, for instance to take top views of the skull, cervical spine, chest, abdomen, and anterior-posterior and/or lateral views of the pelvis. Depending on how the hospital is equipped, these views are taken either with a conventional x-ray unit, partially supplemented by images from a computed tomography (CT) scanner, or the views are taken only with a CT scanner. If both a conventional x-ray unit and a CT scanner are used, the patient must as a rule be transferred from one table to another and moved to a different examination room. After his stay in radiology, the patient often returns to the trauma room for remaining stabilization, before finally being taken to an operating room or to a room in an intensive care unit. The numerous routes between different rooms and/or units of the hospital, and moving the patient from one table to another in every room are both time-consuming and not always wise for the health of the patient in view of his extremely severe injuries. Also, during the examinations and along the way there, it is not always possible to monitor the patient's vital functions continuously and to care for him adequately.

Various systems have become known in which various imaging equipment has been fused or combined into one joint system. From German Patent Disclosure DE 197 11 499 A1, for instance, a radiological diagnostic unit with a CT scanner and an x-ray unit have a common holding device. The holding apparatus is adjustable along a guide rail from a first position, associated with the CT scanner, to a second position, associated with the x-ray unit.

In German Published, Nonexamined Patent Application DE 198 53 463 A1, a plurality of multiple examination systems with many imaging systems have been disclosed; the imaging systems are disposed on a common support and can be associated with the patient's bed by moving the carrier relative to the bed of one of the imaging systems in succession.

U.S. Pat. No. 5,822,814 discloses a diagnosis and/or treatment system that has a C-arm device. The associated table can be pivoted outward 90° to allow a mobile "ring arm CT scanner" to be taken to the table. With this diagnostic and/or treatment system, a full-body scan of the patient is not possible.

German Patent DE 199 21 280 C1 shows a radiological diagnostic unit in which a CT scanner can also be operated as a conventional radiological diagnostic unit, in that the beam emitter that is present for the sake of the computed tomography can be associated with both a row detector for the computed tomography and a further beam receiver.

In a Siemens AG brochure entitled "SOMATOM Emotion, Balance, Esprit-Sliding Gantry", No. A91001-M2120-G151-01-7600, a system comprising a CT scanner and an x-ray unit is also described for angiography. Here, the patient holding apparatus has a table that protrudes past a base on one side. By moving the CT scanner, which is movable along a guide rail on the floor, the protruding part can be introduced into the patient opening of the CT scanner, so that CT images are possible. The angiography device can also be positioned in the region of the protrusion, to take corresponding images.

SUMMARY

These known systems are all oriented toward simplifying examination of the patient but are not suitable for simultaneous treatment, especially for treating patients with multiple traumas, and/or they do not permit full-body scans of the patient.

The object of the invention is a system for medical emergency care and monitoring of a patient that is suitable for both examining and for monitoring and caring for extremely severely injured patients in such a way that the number of times the patient has to be moved from table to table and the travel distances can be kept low, and in which nevertheless a full-body scan is possible.

This object is attained by a system having the following components:

a) a patient holding apparatus with a fixed base and a table mounted on it, and the table protrudes past the base on the head end with a radio transparent first region and on the foot end with a radio transparent second region, b) a CT scanner, which is movable on the floor along a guide element in such a way that the second region of the table can be brought, by moving the CT scanner, into the patient opening of the CT scanner;

c) an x-ray unit, which is arranged for taking x-ray images in the first region of the table; and d) a guided patient board that can slide on the table in the longitudinal direction.

An examination and/or treatment region is created on both sides of the base of the patient holding apparatus, to improve the functional capabilities in terms of care, examination and/or monitoring of the patient. For instance, in the first region that protrudes on the head end, which is also arranged for taking x-ray images, stabilizing the patient is done with life support measures. The patient is accessible there on three sides. As soon as it is found, during the care done there, that a computed tomography image is necessary, the patient is moved, lying on the patient board, along the table to the second region that protrudes on the foot end. By moving the movable CT scanner toward it, the second region can be introduced into the patient opening of the CT scanner, so that corresponding computed tomography images can be made. In a reversal of the usual procedure, the patient is introduced into the computed tomography opening feet first. By means of the guide element of the CT scanner, a slice-by-slice advancement can be performed in such a way that a full-body scan of the patient is possible.

These actions can be done quickly. Transferring the patient from one table to another, which might harm him, is unnecessary. Equally quickly and without being transferred, once the examination has been done in the CT scanner, the patient can be returned to the first region of the table by displacement of the slidable patient board, so that life support actions can be continued there, and/or to take a view of the skull, for instance, by means of the x-ray unit.

The patient board is embodied as slidable on the table, since in this way metal components, which when the patient board is introduced into the patient opening of the CT scanner can cause artifacts in the image, can be largely avoided.

Preferably, the guide rail of the CT scanner and the table are disposed parallel to one another, particularly in a linear arrangement.

In a further feature, the system has a life support unit that can be attached or mounted to the first region of the table and that, in particular, includes at least one respirator and one monitoring device that records vital functions of the patient. A life support unit of this kind can be embodied as a movable trolley ("life support trolley"), for instance. With the life support unit, there is the advantage that both the physiological stabilization of the patient and the diagnostic and treatment work on the severely injured patient can be done without transferring him, with permanent monitoring and care, and in an ergonomically flexible way.

To further shorten the time required caring for the patient (processing time), it is expedient that the patient holding apparatus, the CT scanner, the x-ray unit, and optionally the life support unit are disposed jointly in one room. A trauma room of this kind, for instance in a hospital building, is also the subject of the invention.

Preferably, the second region of the table has at least the length of an adult patient, in particular at least a length of 1.8 meters, or is at least adjustable to such a length. It is thus advantageously possible to examine the patient over his full body length ("height") using the CT scanner. The length of the guide rail of the CT scanner can also be designed for a full-body scan.

For the first region of the table, it is expedient that it has at least half the length of an adult patient, and in particular at least a length of 0.9 meters, or is at least adjustable to such a length. Such a length suffices for instance to take images of the patient with the x-ray unit in the region from his head to approximately his pelvis.

In a preferred refinement, one component of the system is also a patient trolley, which is embodied for receiving the patient board in a fixed way, in particular by positive engagement or coupling. As a result, in situations in which the patient must be brought to or taken away from the system of the invention for medical emergency care and monitoring, it is possible to leave the patient lying on the patient board, and to transfer him along with the patient board gently to the patient trolley.

Especially advantageously, the patient trolley is embodied with support elements for the patient board that are open at the sides in such a way that the table of the patient holding apparatus can be moved underneath such that the patient board received on the patient trolley can be positioned above the table. It is then possible to transfer the patient from the patient trolley to the patient holding apparatus or vice versa by means of slight vertical motions—either by muscle power or driven by a motor—without having to transport the patient sideways or even lift him in a way that is uncomfortable for him and inconvenient for the staff. For this purpose, the support elements of the patient trolley can be adjustable in height, in particular by motor, to make it easier for the staff to work.

The table and/or the patient board are preferably made from carbon-fiber-reinforced plastic. Especially advantageously, the x-ray unit of the system is ceiling-mounted, to keep the first region of the table, especially the region on the floor around the first region, freely usable for the medical staff in the event that the x-ray unit is not needed just at that time. As a result, it is possible for up to four or five persons (anesthesiologist, IV infusion nurse or doctor, radiologist, surgeon, medical record personnel, and so forth) of the medical staff, optionally together with the movable life support unit, to be present near this region all at once. The x-ray unit can be mounted in the ceiling via a rail system, for instance, and can then be movable in the longitudinal direction and/or laterally. For the vertical adjustment, a telescoping stand can be secured to the rail system and carry and x-ray emitter and/or receiver on its end.

The x-ray emitter and the x-ray detector of the x-ray unit are preferably mounted to the ends of two legs of a U-shaped or C-shaped arc, preferably in such a way that views can be taken both from above and below the table.

A work method can be performed, in particular, with the system above. The work method has the following steps:

1) transporting the patient from the ambulance door of a hospital to a trauma room, lying on a patient trolley that has a removable patient board, the patient board being mounted on a rolling frame with support elements that are open at the sides;

2) positioning the patient board above a table of a stationary patient holding apparatus by running the rolling frame under the table with the patient trolley;

3) lowering the patient board onto the table;

4) moving the patient trolley away;

5) to the extent necessary, sliding the patient board with the patient along the table into a radio transparent first region of the table;

6) beginning life-support measures in the first region;

7) optionally, x-ray examination with an x-ray unit associated with the first region;

8) sliding the patient board, with the patient, along the table into a radio transparent second region of the table, preferably with the patient feet first;

9) performing a CT examination in the second region;

10) sliding the patient board with the patient along the table from the second region to the first region, or to an optional third region of the table.

Optionally, in other phases, life support can be continued with further measures in the third region of the table. The third region preferably overlaps a radiopaque, but mechanically stable region, which is supported indirectly or directly by the base of the patient holding apparatus. The first and second regions are located in particular on opposite sides of the third region.

For further preferred features of the patient holding apparatus, and in particular its first region, second region, and third region, as well as of the x-ray unit, CT scanner, or patient trolley, see the remarks made regarding the system in the detailed description below and in the summary above. Also in the work method, a life support unit as described above can be used. In transporting the patient on the patient trolley, the life support unit can preferably be docked—preferably at the head end—to the patient trolley and then in the stationary mode can be moved independently of the patient trolley along the patient holding apparatus. Transporting the patient away from the trauma room can be done analogously, again using the patient trolley.

BRIEF DESCRIPTION OF THE DRAWINGS

One exemplary embodiment of the system according to the invention will be described below in conjunction with FIGS. 1-4. The example also serves to explain the work method of the invention. Shown are.

DETAILED DESCRIPTION OF THE PREFERRED EMBODIMENTS

Figure 1:
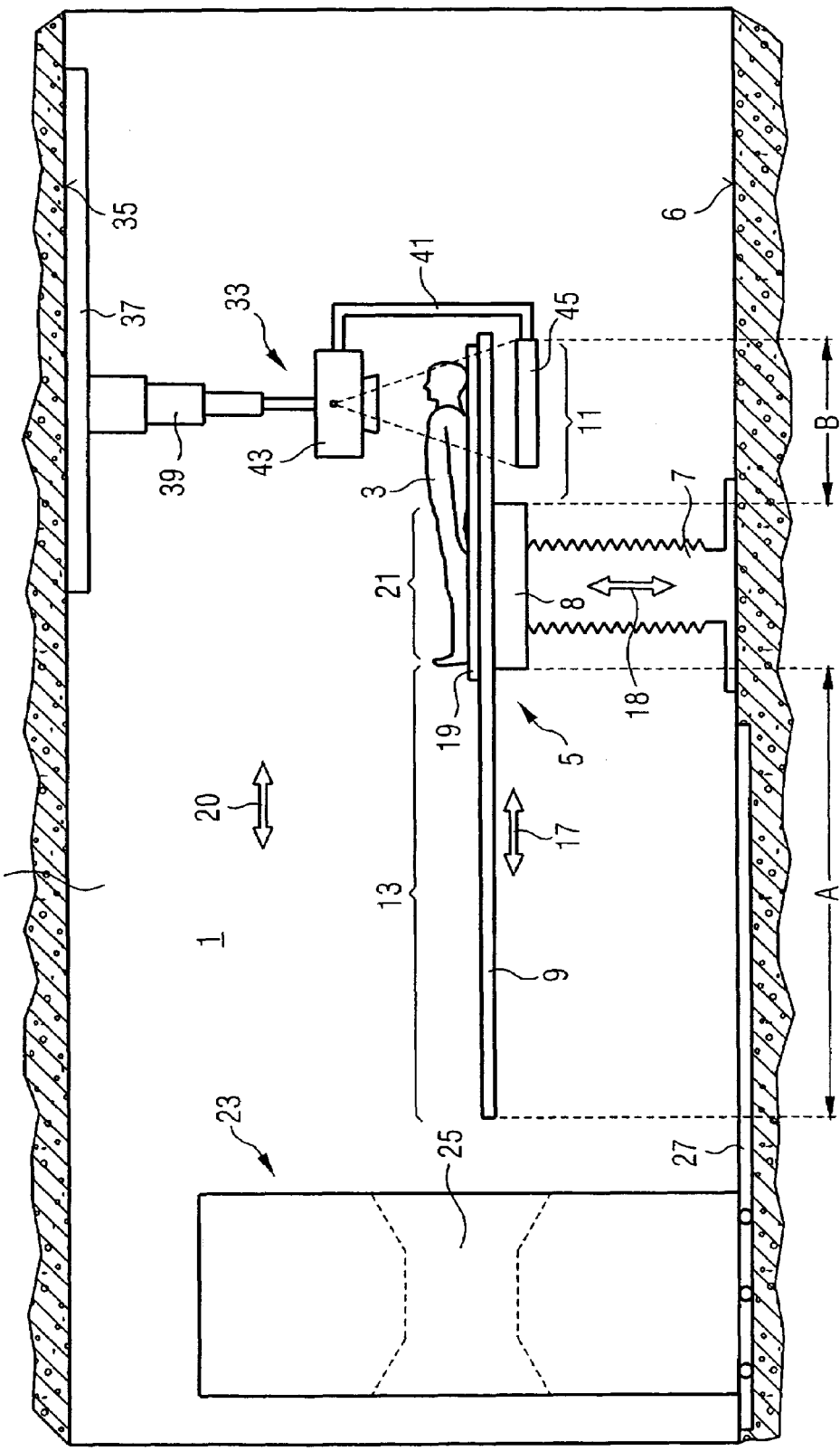
FIG. 1, a schematic longitudinal sectional view of a system according to the invention for medical emergency care and monitoring of a patient.

In FIG. 1, a system 1 for medical emergency care and monitoring of a patient 3 is shown, in which the following components are disposed jointly in one room 4 of a hospital:

A stationary patient holding apparatus 5 with a base 7 secured to the floor 6 of the room 4 in such a way that the base 7 is secure against tilting. The holding apparatus 5 serves to support the patient 3 during his care, monitoring and examination in the room 4. On its upper end, the base 7 has a mechanical mount 8 in which a radio transparent table 9 made of carbon-fiber-reinforced plastic is held. The table 9 protrudes past the base 7 with a radiopaque first region 11 on the head end of the patient and a second radiopaque region 13 on the foot end. The length of the table 9 is approximately 4 meters; the length A of the second region 13 is approximately 2.4 meters, and the length B of the first region 11 is approximately 0.8 meters.

An arrow 17 indicates that the table 9 is movably supported in the mount 8, so that the lengths A, B of the regions 11, 13 can be varied by ±0.6 meters from the values given. Arrow 18 indicates the ability to move the table 9 vertically, which is realized by a suitable mechanical embodiment including a motor in the base 7.

As a further component of the system 1, there is a radio transparent patient board 19, also made of carbon-fiber-reinforced plastic, whose lower edge strips are embodied for sliding longitudinal guidance in the longitudinal direction 20 in the table 9, which is provided with an elongated dish-shaped indentation. The patient 3 can thus be transported back and forth between the regions 11, 13 while lying on the patient board 19. The patient board 19 thus serves as a slide board, in order to put the patient 3 into various process positions without having to be transferred from table to table, for instance into an x-ray position in the first region 11, a computed tomography position in the second region 13, an intubation position, a resuscitation position, and/or a treatment position, these last three being in a central third region 21, which is characterized by widened armrests to make it easier to perform intensive care of the patient 3 and which preferably coincides with the radiopaque but mechanically more-stable region that is supported by the base 7 or the mount 8.

In terms of its shaping, for the sake of artifact-free images, the patient board 19 is embodied by an x-ray unit and a CT scanner.

A radio transparent push button brake can be integrated into the profiled edge strips of the table 9, so that the patient board 19 can be fixed in various positions.

Another component of the system 1 is a CT scanner 23, into whose patient opening 25 the table 9 can be introduced by its second region 13. This introduction is done by moving the CT scanner 23 in the longitudinal direction 20 toward the patient holding apparatus 5 along a guide rail 27 in the floor 6.

As another component, the system 1 has a conventional x-ray unit 33, which is mounted on the ceiling 35 of the room 4. This mounting is done via a rail system 37, which makes it possible to move the x-ray unit 33 away from the first region 11 on the table 9 to allow the medical staff to work unhindered by the x-ray unit 33. The x-ray unit 33 is shown in a position in which a head view of the patient 3 is to be taken in the radio transparent first region 11.

A telescoping stand 39 that can be extended by motor is mounted on the rail system 37, and a U-shaped bracket 41 is supported pivotably and rotatably on its end. In the work position shown, the bracket 41 is pivoted and rotated in such a way that a view from the top can be taken, in which an x-ray emitter 43 projects a beam through the patient 3 from above the table 9, and a through-projection image is taken by an x-ray detector 45 under the table 9. The x-ray detector 45 is a conventional film and plate system, for instance.

Figure 2:
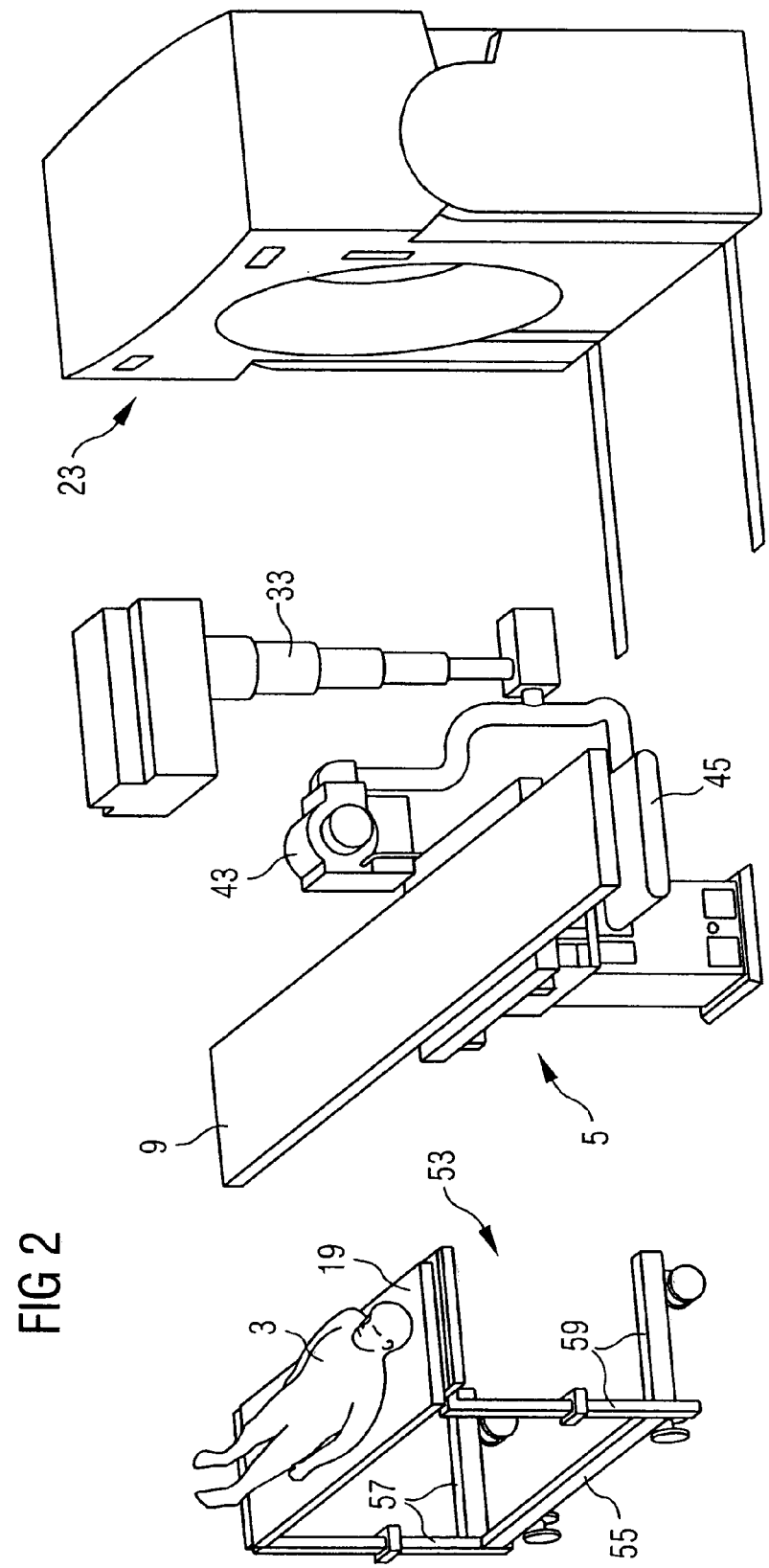
FIG. 2, the system of FIG. 1 in a perspective view in a first work state.

Further components of this system and one possible way of operating the system 1 are described in further detail below in conjunction with FIGS. 2-4. A work method is also described:

In FIG. 2, it is shown how the patient is taken directly from the ambulance door of the hospital, lying on a patient trolley 53, into the trauma room 4. The patient trolley 53 includes a base part 55, which has four rollers and has the form of a U open at the side. The lateral support elements 57, 59 that serve to carry the patient board 19 have one crossbeam or base part 55, one vertical column originating at it, and another vertical cross girder adjoining it at the top. Both the base part 55 and the support elements 57, 59 are open at the side, so that the patient trolley 53 can be slid under the table 9 with the base part 55, both in the first region 11, the second region 13, and including the base 7 of the patient holding apparatus 5, so that the patient 3 can be positioned, lying on the patient board 19, over the table 9. In such a position, the adjustable-height support elements 57, 59 of the patient trolley 53 are lowered, until the patient board 19 comes to rest on the table 9. The patient trolley 53, in the embodiment shown, is a component of the system 1 and is adapted to the other components in terms of compatibility, functions, and/or dimensions. The patient board 19 is embodied such that it is both fixable to the patient trolley 53 and slidable along the table 9.

Figure 3:
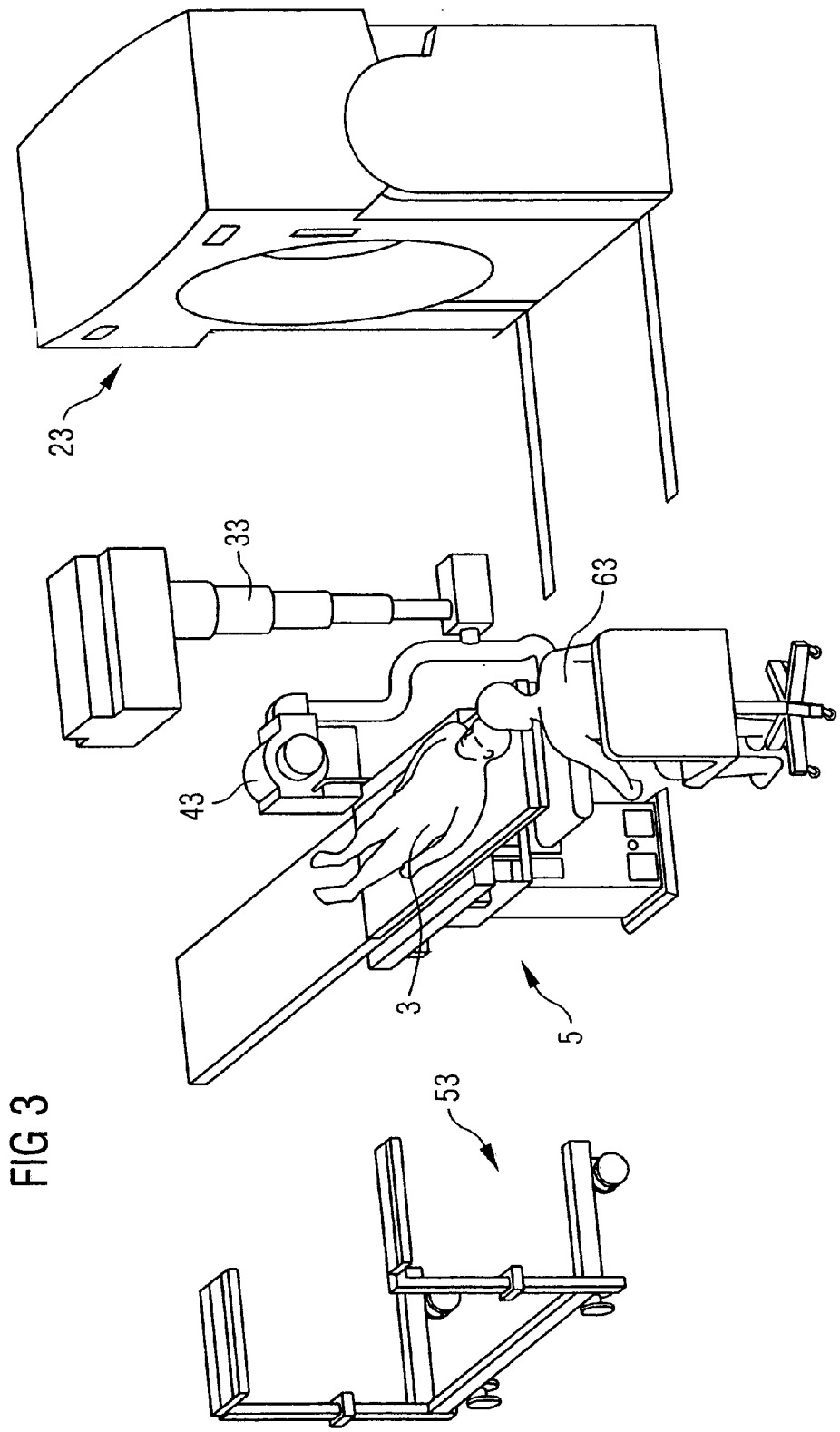
FIG. 3, the system of FIG. 1 in a perspective view in a second work state.

In FIG. 3, one process phase of the method performed at the system 1 is shown, in which the patient board 19 together with the patient 3 has already been taken off the trolley 53 and placed on the table 9. For space-saving accommodation of the system 1 in the room 4, it can be advantageous, if—as suggested in FIGS. 2 and 3—the table 9 of the patient holding apparatus 5 is supported rotatably on the base 7 about a vertical axis.

It is also indicated in FIG. 3 how care of the patient 3 by the medical staff 63, and in particular an anesthesiologist, is begun in the first region 11 and at the same time an x-ray image is made.

Figure 4:
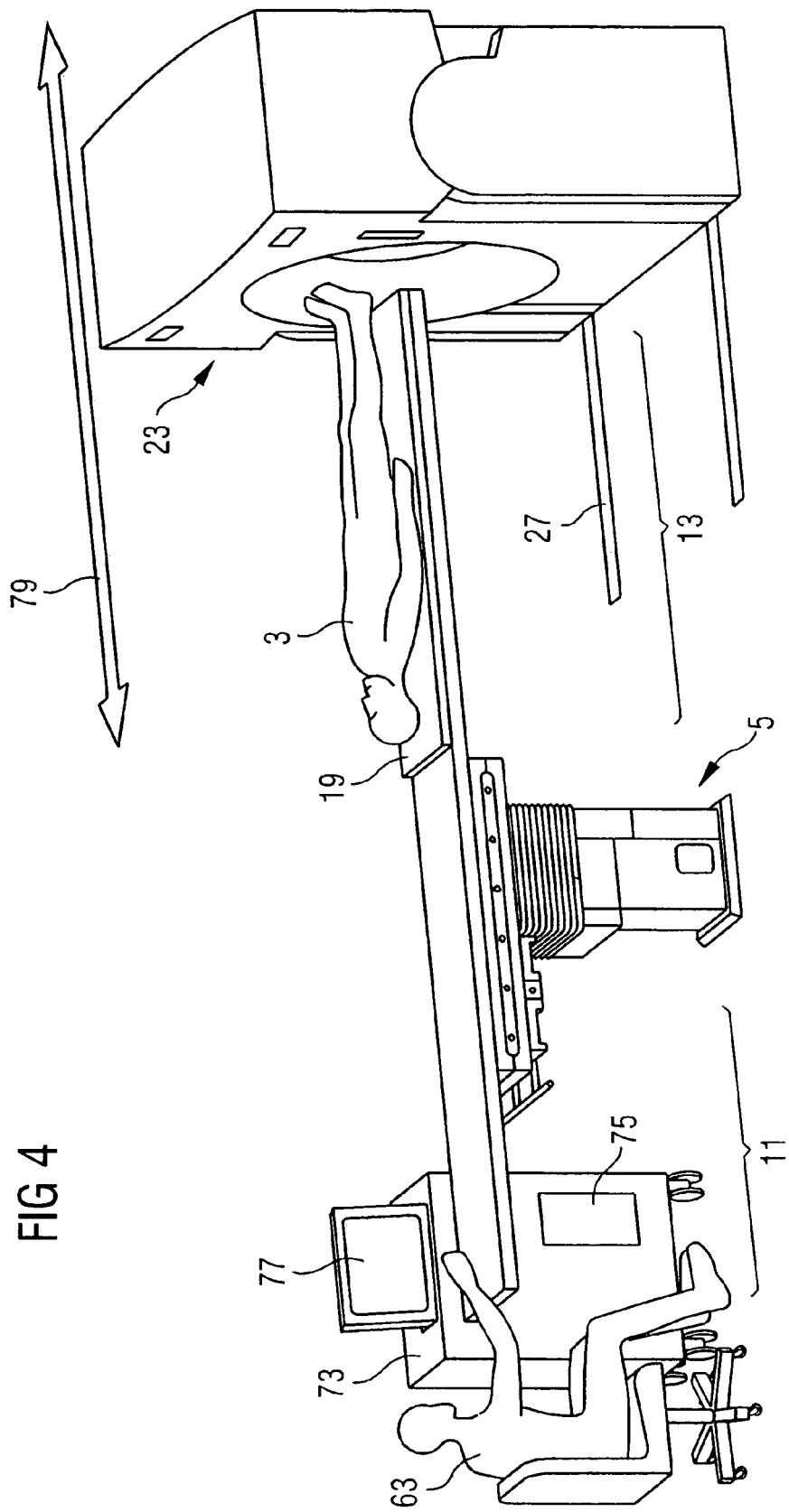
FIG. 4, the system of FIG. 1 in a perspective view in a third work state.

In the work phase shown in FIG. 4, the table 9 has been rotated 90° relative to the position in FIG. 3 and oriented parallel to the guide elements 27 of the CT scanner 23. To support the work of the anesthesiologist 63 and an IV infusion nurse, not shown, there is also a life support unit 73, which is embodied as a movable carriage. The life support unit 73, which in the exemplary embodiment is also a component of the system 1, has a respirator 75 with an oxygen bottle, not identified by a reference numeral. There is also a monitoring device 77 for recording vital functions of the patient 3, in particular an electrocardiography device (EKG). There can also be mounts on the life support unit 73 for auxiliary devices for IV infusions, transfusions and perfusion studies.

In the situation shown in FIG. 4, the medical staff 63 has just now realized that an examination with the CT scanner 23 is necessary. For that purpose, the patient 3 has been moved, sliding on the patient board 19, into the second region 13, and the life support unit 73 can—if necessary—be carried along on the side. For a scanning examination with the CT scanner 23, the CT scanner is then moved along the guide elements 27 in the floor 6 in the longitudinal direction 79 over the patient 3 to a length of up to 2 m. Then, the CT scanner 23 moves back into its parking position, and other scans can then be performed as needed.

After the examination by the CT scanner 23, the patient 3, with the patient board 19 embodied as a slide board, is pushed up to the head end of the table 9, for instance to continue the life-support measures and/or to use the x-ray unit 33.

Once the process steps in room 4 have been completed, the patient trolley 53 is moved up from the side with its U-shaped support elements 57, 59, and the patient board 19 together with the patient 3 is transferred to the patient trolley 53. The life support unit 73 is docked, preferably on the head end, to the patient trolley 53 and moved away, together with the patient 3 who is thus being continuously cared for and monitored.

With the system 1, the diagnostic and treatment process for the patient 3 can be performed entirely on a single patient holding apparatus 5. Hence there are no unnecessary transfers of the patient, nor does he have to be transported to possibly farther-away examination areas. On the contrary, in the system 1, the devices relevant for imaging, especially the CT scanner 23 and the conventional x-ray unit 33, can be brought from their respective parking positions to the patient holding apparatus 5 and then, after the images have been taken, returned to their parking positions. It is thus attained that the transport times to the various examination areas that are usual today, along with the transfers from one table to another are dispensed with. This gain in time can be decisive in caring for patients with multiple traumas.

The invention claimed is:

1. A system for medical emergency care and monitoring of a patient, the system comprising:
a patient holding apparatus with a fixed base and a table mounted on the fixed base, the table protruding simultaneously past a portion of the fixed base movably supporting the table on a head end with a radio transparent first region and on a foot end with a radio transparent second region, the foot end on an opposite side of the fixed base relative to the head end;
a CT scanner which is movable along a guide element in such a way that the second region of the table is operable to be brought, by moving the CT scanner, into a patient opening of the CT scanner;
an x-ray unit which is arranged for taking X-ray images in the first region of the table protruding past the portion of the fixed base movably supporting the table; and
a guided patient board that is adaptively configured to be accepted by the table and that is operable to slide on the table in a longitudinal direction such that the guided patient board can be positioned at a first imaging position and a second imagine position, the first imaging position being over the radio transparent first region of the table and the second imaging position being over the radio transparent second region of the table, the radio transparent first and second regions of the table both remaining protruding simultaneously past the fixed base on the head end and the foot end, respectively, for both the first and second imaging positions.

2. The system of claim 1 in which the guide element of the CT scanner and the table are disposed parallel to one another in a linear arrangement.

3. The system of claim 1 further comprising a life support unit mounted or attachable in the first region of the table, the life support unit including at least one respirator and a monitoring device operable to record a vital function of the patient.

4. The system of claim 1 in which the second region of the table comprises at least the length of an adult patient or is at least adjustable to such a length.

5. The system of claim 1 in which the first region of the table has at least half the length of an adult patient or is at least adjustable to such a length.

6. The system of claim 1 in which the patient holding apparatus, CT scanner, and x-ray unit are all disposed in one room.

7. The system of claim 1 further comprising a patient trolley operable to hold the patient board.

8. The system of claim 7 in which the patient trolley has two support elements for the patient board that are open at the sides in such a way that the table of the patient holding apparatus is operable to be moved underneath the patient board on the patient trolley.

9. The system of claim 8 in which the support elements of the patient trolley are adjustable in height.

10. The system of claim 1 in which at least one of the table and the patient board are made from carbon-fiber-reinforced plastic.

11. The system of claim 1 in which the x-ray unit is ceiling-mounted.

12. A system for medical emergency care and monitoring of a patient, the system comprising:
a patient holding apparatus with a fixed base having a mechanical mount, the mechanical mount being operable to movably support a table vertically, the table protruding simultaneously past the mechanical mount on a head end with a radio transparent first region and on a foot end with a radio transparent second region, the foot end on an opposite side of the mechanical mount relative to the head end;
a CT scanner which is movable along a guide element in such a way that the second region of the table is operable to be brought, by moving the CT scanner, into a patient opening of the CT scanner;
an x-ray unit which is arranged for taking X-ray images in the first region of the table; and
a guided patient board that is adaptively configured to be accepted by the table and that is operable to slide along the table in a longitudinal direction such that the guided patient board can move into a first imaging position and a second imaging position, the table remaining protruding simultaneously past the mechanical mount on the head end and the foot end in both the first and second imaging positions, the guided patient board being positioned over the radio transparent first region of the table at the first imaging position and positioned over the radio transparent second region of the table at the second imaging position.

13. The system of claim 12, wherein the guide element of the CT scanner and the table are disposed parallel to one another in a linear arrangement, and the table comprises a brake operable to lock the guided patient board into various longitudinal positions alone the table.

14. The system of claim 12, wherein the table includes a third region between the first region and the second region having widened armrests as compared with the first region and the second region.

15. The system of claim 12, wherein the x-ray unit comprises a ceiling mounted U-shaped bracket for holding an X-ray emitter and an X-ray detector.

16. A system for medical emergency care and monitoring of a patient, the system comprising:
- a patient holding apparatus with a fixed base and a table mounted on the fixed base, the table protruding simultaneously past a portion of the fixed base movably supporting the table on a head end with a radio transparent first region and on a foot end with a radio transparent second region, the foot end on an opposite side of the fixed base relative to the head end, the first region and the second region being separated by a third region of the table having widened armrests as compared with the first region and the second region to facilitate treatment of the patient;
- a CT scanner which is movable along a guide element in such a way that the second region of the table is operable to be brought, by moving the CT scanner, into a patient opening of the CT scanner;
- an x-ray unit which is arranged for taking X-ray images in the first region of the table, the x-ray unit being a ceiling mounted device comprising a U-shaped bracket for holding an X-ray emitter and an X-ray detector; and
- a guided patient board that is adaptively configured to be accepted by the table and that is operable to slide on the table in a longitudinal direction.

17. The system of claim 16, wherein the x-ray unit is ceiling mounted via a rail system, and wherein the rail system is operable to move the x-ray unit away from the first region.

18. The system of claim 17, wherein the rail system comprises a telescoping stand, the telescoping stand being operable to move the x-ray unit vertically.

19. The system of claim 16, wherein the U-shaped bracket is pivoted and rotated in a such a manner that an image from above the first region is acquired via the x-ray emitter projecting a beam through the first region from above the table to the x-ray detector positioned under the table.

20. The system of claim 19, further comprising a life support unit associated with the table, the life support unit including at least one respirator and a monitoring device operable to record a vital function of the patient.

* * * * *